United States Patent
Frade Lopez (10) Patent No.: US 9,567,384 B2
(45) Date of Patent: Feb. 14, 2017

(54) PHOSPHORYLATION ON THE THR-248 AND/OR THR-250 RESIDUES OF TRANSCRIPTION FACTOR E2F4 AS A THERAPEUTIC TARGET IN PATHOLOGICAL PROCESSES ASSOCIATED WITH SOMATIC POLYPLOIDY

(71) Applicant: CONSEJO SUPERIOR DE INVESTIGACIONES CIENTIFICAS (CSIC), Madrid (ES)

(72) Inventor: Jose Maria Frade Lopez, Madrid (ES)

(73) Assignee: Consejo Superior de Investigaciones Cientificas (CSIC), Madrid (ES)

( * ) Notice: Subject to any disclaimer, the term of this patent is extended or adjusted under 35 U.S.C. 154(b) by 0 days.

(21) Appl. No.: 14/352,584

(22) PCT Filed: Nov. 15, 2012

(86) PCT No.: PCT/ES2012/070795
§ 371 (c)(1),
(2) Date: Apr. 17, 2014

(87) PCT Pub. No.: WO2013/076331
PCT Pub. Date: May 30, 2013

(65) Prior Publication Data
US 2015/0018278 A1 Jan. 15, 2015

(30) Foreign Application Priority Data

Nov. 24, 2011 (ES) .................................. 201131892

(51) Int. Cl.

| | |
|---|---|
| *A61K 38/00* | (2006.01) |
| *A61K 38/16* | (2006.01) |
| *A61P 3/04* | (2006.01) |
| *A61P 25/00* | (2006.01) |
| *A61P 25/28* | (2006.01) |
| *C07K 1/00* | (2006.01) |
| *C07K 14/00* | (2006.01) |
| *C07K 17/00* | (2006.01) |
| *C07K 14/47* | (2006.01) |
| *A61K 38/17* | (2006.01) |

(52) U.S. Cl.
CPC ....... *C07K 14/4702* (2013.01); *A61K 38/1709* (2013.01); *A61K 38/00* (2013.01)

(58) Field of Classification Search
None
See application file for complete search history.

(56) References Cited

U.S. PATENT DOCUMENTS 6,303,335 B1    10/2001 Bernards et al.

FOREIGN PATENT DOCUMENTS

| WO | 2004026246 A2 | 4/2004 |
| WO | WO 2010/069074 | 6/2010 |

OTHER PUBLICATIONS

American Heritage® Dictionary of the English Language, Fifth Edition. (2011). Retrieved Jun. 23, 2015 from http://www.thefreedictionary.com/prevent.*
Erenpreisa et al., Oncoscience 2:3-14 (2015).*
Iourov et al., Current Genomics 11:387-396 (2010).*
Kim et al., Biochim. Biophys. Acta 1802:396-405 (2010).*
Lopez-Sanchez, et al., Handbook of Neurotoxicity, Kostrzewa, R.M., ed., Springer-Science & Business Media, New York, NY, pp. 1877-1897 (2014).*
Miyawaki et al., Geriatric Nephrology Curriculum, American Society of Nephrology, pp. 1-5 (2009).*
Munoz et al., Neuropharmacology 58:561-568 (2010).*
Storchova et al., Molec. Cell Biol. 5:45-54 (2004).*
"The Mouse as a Model System", available online at http://ko.cwru.edu/info/mousemodel.html, 4 pages, (2013).*
"Base De Dates [online]", UniProtKB/TrEMBL. Access No. G3TWT5. Retrieved from the internet<http://www.uniprot.org/uniprot/G3TWT5> viewed on Apr. 16, 2014.
"Boletin CESEAND. Perfiles tecnologicos. Bio-Salud [botetin online].", Europe Network Partnership tools & CESEAND, Mar. 2012, Boletin No. 70. Retrieved from the internet:<http://www.reta.es/attachments/article/10635/120301_Bol_BIO.pdf> viewed on Apr. 16, 2014.
Chang, et al., "Crystal structures of MAP Kinase p38 complexed to the docking sites on its nuclear substrate MEF2A and activator MKK3b.", Molecular Cell. 2002, vol. 9 pp. 1241-1249.
Deschenes, et al., "The Nucleocytoplasmic shutlling of E2F4 is involved in the regulation of human intestinal epthelial cell proliferation and differentiation.", Journal of Cellular Physiology. 2004, pp. 262-273.
Frade, et al., "A novel hypothesis for Alzheimer disease based on neuronal tetraploidy induced by p75NTR", Cell Cycle 9:10, 1934-1941; May 15, 2010.
McCrann, et al., "Vascular Smooth Muscle Cell Polyploidy: An Adaptive or Maladaptive Response?", J. Cell. Physiol. 215:588-592, 2008, 588-592.
Morillo, et al., "Nerve Growth factor-induced cell cycle reentry in newborn neurons is triggered by p38 MAPK-dependent E2F4 phosphorylation.", Molecular and Cellular Biology. Jul. 2012, vol. 32(14) pp. 2722-27237.
Morillo, et al., "Somatic tetraploidy in specific chick retinal ganglion cells induced by nerve growth factor", PNAS, Jan. 5, 2010, vol. 107, No. 1, pp. 109-114.

(Continued)

*Primary Examiner* — Hasan Ahmed
*Assistant Examiner* — Thea D'Ambrosio
(74) *Attorney, Agent, or Firm* — Kramer Amado P.C.

(57) ABSTRACT

The object of the invention is based on inhibiting specific phosphorylation on Thr248 and/or Thr250 residues of human transcription factor E2F4 to inhibit somatic endoreduplication processes in postmitotic cells which may be associated with various pathological conditions. The invention covers all currently known methods for the specific inhibition of protein phosphorylation (including the expression of mutant forms of E2F4 without Thr residues phosphorylated by p38MAPK) or methods developed in the future that may be applied to Thr-248 and/or Thr-250 residues of human transcription factor E2F4.

16 Claims, 5 Drawing Sheets

(56) References Cited

OTHER PUBLICATIONS

Mosch, et al., "Aneuploidy ad DNA replication in the normal human brain and Alzheimer's disease.", The Journal of Neuroscience. 2007, vol. 27 (26) pp. 6859-6867.
Ullah, et al., "Developmentally programmed endoreduplication in animals", Cell Cycle May 15, 2009; 8(10); 1501-1509.
Vliegen, et al., "Polyploidy of Myocte Nuclei in Pressure Overloaded Human Hearts: A Flow Cytometric Study in Left and Right Ventricular Myocardium", The American Journal of Cardiovascular Pathology. vol. 5, No. 1, 1994, 27-31.
Yabe, at al., "Changes in DNA Synthesis in Significantly Hypertrophied Human Cardiac Muscle", Advances in Myocardiology, vol. 1, 1980, 553-563.
Yang, "Neuronal Cell Death Is Preceded by Cell Cycle Events at All Stages of Alzheimer's Disease", The Journal of Neuroscience, Apr. 1, 20013. 203(7):, 2557-2563.
"European Search Report for EP12851300 dated Jun. 1, 2015".
Barone, et al., "SB 239063, a Second-Generation p38 Mitrogen-Activated Protein Kinase Inhibitor, REduces Brain Injury and Neurological Deficits in Cerebral Focal Ishemia", The Journal of Pharmacology and Experimental Therapeutics, vol. 196, No. 2, Jan. 1, 2001, pp. 312-321.
Kitazawa, et al., "Blocking IL-1 Signaling Rescues Cognition, Attenuates Tau Pathology, and Restores Neuronal-Catenin pathway Function in an Alzheimer's Disease Model", The Journal of Immunology, vol. 187, No. 12, Nov. 16, 2011, pp. 6539-6549
Mehan, et al., "Effect of Mitogen Activated Protein Kinase Inhibitor in Animal Model of Alzheimer's Diseases", Jan. 1, 2011, p. 212, Retrieved from the internet: [http://www.researchgate.net/publication/216026424_EFFECT_OF_MITOGEN_ACTIVATED_PROTEIN_KINASE_INHIBITOR_IN_ANIMAL_MODEL_OF_ALZHEIMERS_DISEASES] [retrieved May 20, 2015].
Munoz, et al., "Targeting p38 MAPK pathway for the treatment of Alzheimer's disease", Neuropharmacology, vol. 58, No. 3, Mar. 1, 2010, pp. 561-568.
Machine Translation of the International Search Report PCT/ES2012/070795, Feb. 28, 2013.
Burns, et al., "Nestin-CreER Mice Reveal DNA Synthesis by Nonapoptotic Neurons following Cerebral Ischemia-Hypoxia", Cerebral Cortex, Nov. 2007.
Cooper, et al., "Peptide Derived from HIV-1 TAT Protei nDestabilizes a Monolayer of Endothelial Cells in an in vitro Mode of the Blood-Brain Barrier and Allows Permeation of High Molecular Weight Proteins", The Journal of Biological Chemistry, vol. 238, No. 53, pp. 44676-44683, Dec. 28, 2012.
Haynes, "The bromodomain: a conserved sequence found in human, Drosophila and yeast proteins", Nucleic Acids Research, vol. 20, No. 10, 1992.
Hoglinger, et al., "The pRb/E2F cell-cycle pathway mediates cell death in Parkinson's disease", PNAS, Feb. 2007, vol. 104, 3585-3590.
Kaech, et al., "Culturing hippocampal neurons", Nature Protocols, vol. 1, No. 5, 2006.
Lopez-Sanchez, et al., "Genetic Evidence for P75ntr-Dependent Tetraploidy in Cortical Projection Neurons from Adult Mice", The Journal of Neuroscience, Apr. 24, 2013, 33(17): 7488-7500.
Tucker, "Neurotrophins are required for nerve growth during development", Nature Neuroscience, vol. 4, No. 1, Jan. 2001.
Haney, "Exosomes as drug delivery vehicles for Parkinson's disease therapy", Journal of Controlled Release 207 (2015) 18-30.
Wang, "Delivery of therapeutic agents by nanoparticles made of grapefruit-derived lipids", Nature Communications 4:1867, 13 pages, (2013).

* cited by examiner

SEQUENCE LISTING

```
<160> NUMBER OF SEQ ID NOS: 10

<210> SEQ ID NO 1
<211> LENGTH: 413
<212> TYPE: PRT
<213> ORGANISM: Homo sapiens

<400> SEQUENCE: 1

Met Ala Glu Ala Gly Pro Gln Ala Pro Pro Pro Gly Thr Pro Ser
1               5                   10                  15

Arg His Glu Lys Ser Leu Gly Leu Leu Thr Thr Lys Phe Val Ser Leu
                20                  25                  30

Leu Gln Glu Ala Lys Asp Gly Val Leu Asp Leu Lys Leu Ala Ala Asp
            35                  40                  45
```

```
Thr Leu Ala Val Arg Gln Lys Arg Ile Tyr Asp Ile Thr Asn Val
    50                  55                  60

Leu Glu Gly Ile Gly Leu Ile Glu Lys Ser Lys Asn Ser Ile Gln
65                  70                  75                  80

Trp Lys Gly Val Gly Pro Gly Cys Asn Thr Arg Glu Ile Ala Asp Lys
                85                  90                  95

Leu Ile Glu Leu Lys Ala Glu Ile Glu Glu Leu Gln Gln Arg Glu Gln
                100                 105                 110

Glu Leu Asp Gln His Lys Val Trp Val Gln Gln Ser Ile Arg Asn Val
            115                 120                 125

Thr Glu Asp Val Gln Asn Ser Cys Leu Ala Tyr Val Thr His Glu Asp
130                 135                 140

Ile Cys Arg Cys Phe Ala Gly Asp Thr Leu Leu Ala Ile Arg Ala Pro
145                 150                 155                 160

Ser Gly Thr Ser Leu Glu Val Pro Ile Pro Glu Gly Leu Asn Gly Gln
                165                 170                 175

Lys Lys Tyr Gln Ile His Leu Lys Ser Val Ser Gly Pro Ile Glu Val
                180                 185                 190

Leu Leu Val Asn Lys Glu Ala Trp Ser Ser Pro Val Ala Val Pro
            195                 200                 205

Val Pro Pro Glu Asp Leu Leu Gln Ser Pro Ser Ala Val Ser Thr
210                 215                 220

Pro Pro Pro Leu Pro Lys Pro Ala Leu Ala Gln Ser Gln Glu Ala Ser
225                 230                 235                 240

Arg Pro Asn Ser Pro Gln Leu Thr Pro Thr Ala Val Pro Gly Ser Ala
                245                 250                 255

Glu Val Gln Gly Met Ala Gly Pro Ala Ala Glu Ile Thr Val Ser Gly
            260                 265                 270

Gly Pro Gly Thr Asp Ser Lys Asp Ser Gly Glu Leu Ser Ser Leu Pro
        275                 280                 285

Leu Gly Pro Thr Thr Leu Asp Thr Arg Pro Leu Gln Ser Ser Ala Leu
    290                 295                 300

Leu Asp Ser Ser Ser Ser Ser Ser Ser Ser Ser Ser Ser Ser Ser Asn
305                 310                 315                 320

Ser Asn Ser Ser Ser Ser Gly Pro Asn Pro Ser Thr Ser Phe Glu
                325                 330                 335

Pro Ile Lys Ala Asp Pro Thr Gly Val Leu Glu Leu Pro Lys Glu Leu
            340                 345                 350

Ser Glu Ile Phe Asp Pro Thr Arg Glu Cys Met Ser Ser Glu Leu Leu
        355                 360                 365

Glu Glu Leu Met Ser Ser Glu Val Phe Ala Pro Leu Leu Arg Leu Ser
    370                 375                 380

Pro Pro Pro Gly Asp His Asp Tyr Ile Tyr Asn Leu Asp Glu Ser Glu
385                 390                 395                 400

Gly Val Cys Asp Leu Phe Asp Val Pro Val Leu Asn Leu
                405                 410

<210> SEQ ID NO 2
<211> LENGTH: 410
<212> TYPE: PRT
<213> ORGANISM: Mus musculus

<400> SEQUENCE: 2

Met Ala Glu Ala Gly Pro Gln Ala Pro Pro Pro Gly Thr Pro Ser
1               5                   10                  15
```

```
Arg His Glu Lys Ser Leu Gly Leu Leu Thr Thr Lys Phe Val Ser Leu
                20                  25                  30

Leu Gln Glu Ala Lys Asp Gly Val Leu Asp Leu Lys Leu Ala Ala Asp
            35                  40                  45

Thr Leu Ala Val Arg Gln Lys Arg Arg Ile Tyr Asp Ile Thr Asn Val
 50                  55                  60

Leu Glu Gly Ile Gly Leu Ile Glu Lys Ser Lys Asn Ser Ile Gln
 65                  70                  75                  80

Trp Lys Gly Val Gly Pro Gly Cys Asn Thr Arg Glu Ile Ala Asp Lys
                85                  90                  95

Leu Ile Glu Leu Lys Ala Glu Ile Glu Glu Leu Gln Gln Arg Glu Gln
                100                 105                 110

Glu Leu Asp Gln His Lys Val Trp Val Gln Gln Ser Ile Arg Asn Val
            115                 120                 125

Thr Glu Asp Val Gln Asn Ser Cys Leu Ala Tyr Val Thr His Glu Asp
130                 135                 140

Ile Cys Arg Cys Phe Ala Gly Asp Thr Leu Leu Ala Ile Arg Ala Pro
145                 150                 155                 160

Ser Gly Thr Ser Leu Glu Val Pro Ile Pro Glu Gly Leu Asn Gly Gln
                165                 170                 175

Lys Lys Tyr Gln Ile His Leu Lys Ser Met Ser Gly Pro Ile Glu Val
            180                 185                 190

Leu Leu Val Asn Lys Glu Ala Trp Ser Ser Pro Val Ala Val Pro
            195                 200                 205

Val Pro Pro Asp Asp Leu Leu Gln Ser Pro Pro Ala Val Ser Thr
210                 215                 220

Pro Pro Pro Leu Pro Lys Pro Ala Leu Ala Gln Pro Gln Glu Ser Ser
225                 230                 235                 240

Pro Pro Ser Ser Pro Gln Leu Thr Thr Pro Thr Pro Val Leu Gly Ser
                245                 250                 255

Thr Gln Val Ser Glu Val Ala Cys Gln Thr Ser Glu Ile Ala Val Ser
            260                 265                 270

Gly Ser Pro Gly Thr Glu Asn Lys Asp Ser Gly Glu Val Ser Ser Leu
            275                 280                 285

Pro Leu Gly Leu Thr Ala Leu Asp Thr Arg Pro Leu Gln Ser Ser Ala
290                 295                 300

Leu Leu Asp Ser Ser Ser Ser Ser Ser Ser Ser Ser Ser Ser Ser Ser
305                 310                 315                 320

Ser Ser Ser Ser Gly Pro Asn Pro Ser Thr Ser Phe Glu Pro Ile Lys
                325                 330                 335

Ala Asp Pro Thr Gly Val Leu Asp Leu Pro Lys Glu Leu Ser Glu Ile
            340                 345                 350

Phe Asp Pro Thr Arg Glu Cys Met Ser Ser Glu Leu Leu Glu Glu Leu
            355                 360                 365

Met Ser Ser Glu Val Phe Ala Pro Leu Leu Arg Leu Ser Pro Pro Pro
        370                 375                 380

Gly Asp His Asp Tyr Ile Tyr Asn Leu Asp Glu Ser Glu Gly Val Cys
385                 390                 395                 400

Asp Leu Phe Asp Val Pro Val Leu Lys Leu
                405                 410

<210> SEQ ID NO 3
<211> LENGTH: 414
```

<212> TYPE: PRT
<213> ORGANISM: Gallus gallus

<400> SEQUENCE: 3

```
Met Ala Glu Cys Gly Pro Gln Pro Gly Ala Gly Gly Gly Gly
1               5                   10                  15

Gly Gly Gly Gly Gly Ser Gly Gly Ala Gly Ala Pro Ser Arg His
            20                  25                  30

Glu Lys Ser Leu Gly Leu Leu Thr Thr Lys Phe Val Ser Leu Leu Gln
            35                  40                  45

Glu Ala Lys Asp Gly Val Leu Asp Leu Lys Leu Ala Ala Asp Thr Leu
50                  55                  60

Ala Val Arg Gln Lys Arg Ile Tyr Asp Ile Thr Asn Val Leu Glu
65                  70                  75                  80

Gly Ile Gly Leu Ile Glu Lys Lys Ser Lys Asn Ser Ile Gln Trp Lys
                85                  90                  95

Gly Val Gly Pro Gly Cys Asn Thr Arg Glu Ile Ala His Lys Leu Ile
            100                 105                 110

Glu Leu Lys Ala Asp Ile Glu Asp Leu Glu Gln Gln Glu Gln Glu Leu
            115                 120                 125

Glu Lys Gln Lys Met Trp Val Gln Gln Ser Ile Lys Asn Val Thr Glu
130                 135                 140

Asp Val Gln Asn Asn Trp Leu Ala Tyr Val Thr His Glu Asp Ile Cys
145                 150                 155                 160

Lys Cys Phe Thr Gly Asp Thr Leu Leu Ala Ile Arg Ala Pro Ser Gly
                165                 170                 175

Thr Arg Leu Glu Val Pro Ile Pro Glu Gly Pro Ser Arg Gln Lys Lys
            180                 185                 190

Tyr Gln Ile His Leu Lys Ser Thr Ser Gly Pro Ile Asp Val Leu Leu
            195                 200                 205

Val Asn Lys Asp Ala Trp Ser Ser Pro Pro Val Val Leu Pro Val Pro
210                 215                 220

Pro Pro Glu Asp Leu Ile Gln Cys Gln Ala Val Ala Pro Ser Lys Pro
225                 230                 235                 240

Gln Ile Pro Pro Leu Ala His Phe Gln Glu Ala Ser Val Pro Ser Ser
                245                 250                 255

Thr Gln Pro Ser Thr Pro Thr Pro Ser Ser Thr Gln Asp His Ser Pro
            260                 265                 270

Pro Glu Gln Lys Asp Thr Ser Thr Glu Cys Ser Ile Ser Val Val Glu
            275                 280                 285

Ser Lys Ser Ser Ser Ser Asp Leu Asp Pro Leu Ser Asn Val Ser Ala
290                 295                 300

Pro Ser Gly His Thr Ala Arg Leu Asp Thr Gln Leu Leu Gln Ser Ser
305                 310                 315                 320

Ala Ser Leu Asp Ser Ser Val Leu Pro Ser Pro Ser Ala Ser Phe
                325                 330                 335

Glu Pro Ile Lys Pro Asp Pro Ala Gly Met Leu Glu Leu Pro Lys Glu
            340                 345                 350

Leu Ser Glu Met Phe Asp Pro Thr Arg Glu Cys Met Asn Ser Glu Leu
            355                 360                 365

Leu Glu Glu Leu Met Ser Ser Glu Val Phe Ala Pro Leu Leu Arg Leu
370                 375                 380

Ser Pro Pro Pro Gly Asp His Asp Tyr Ile Tyr Asn Leu Asp Glu Ser
385                 390                 395                 400
```

Glu Gly Val Cys Asp Leu Phe Asp Val Pro Val Leu Asn Leu
                405                 410

<210> SEQ ID NO 4
<211> LENGTH: 1242
<212> TYPE: DNA
<213> ORGANISM: Homo sapiens

<400> SEQUENCE: 4
atggcggagg ccgggccaca ggcgccgccg cccccgggca ctccaagccg gcacgaaaag      60
agcctgggac tgctcaccac caagttcgtg tcccttctgc aggaggccaa ggacggcgtg     120
cttgacctca agctggcagc tgacacccta gctgtacgcc agaagcggcg gatttacgac     180
attaccaatg tttggaagg tatcgggcta atcgagaaaa agtccaagaa cagcatccag     240
tggaagggtg tggggcctgg ctgcaatacc cgggagattg ctgacaaact gattgagctc     300
aaggcagaga tcgaggagct gcagcagcgg gagcaagaac tagaccagca caaggtgtgg     360
gtgcagcaga gcatccggaa cgtcacagag gacgtgcaga cagctgtttt ggcctacgtc     420
actcatgagg acatctgcag atgctttgct ggagataccc tcttggccat ccgggcccca     480
tcaggcacca gctggaggt gcccatccca gagggtctca atgggcagaa gaagtaccag     540
attcacctga agagtgtgag tggtcccatt gaggttctgc tggtgaacaa ggaggcatgg     600
agctcacccc ctgtggctgt gcctgtgcca ccacctgaag atttgctcca gagcccatct     660
gctgtttcta cacctccacc tctgcccaag cctgccctag cccagtccca ggaagcctca     720
cgtccaaata gtcctcagct cactcccact gctgtccctg gcagtgcaga agtccaggga     780
atggctggcc cagcagctga gatcacagtg agtggcggcc ctgggactga tagcaaggac     840
agtggtgagc tcagttcact cccactgggc ccaacaacac tggacacccg gccactgcag     900
tcttctgccc tgctggacag cagcagcagc agcagcagca gcagcagcag cagcagcaac     960
agtaacagca gcagttcgtc cggacccaac ccttctacct cctttgagcc catcaaggca    1020
gaccccacag gtgttttgga actccccaaa gagctgtcag aaatctttga tcccacacga    1080
gagtgcatga gctcggagct gctggaggag ttgatgtcct cagaagtgtt tgcccctctg    1140
cttcgtcttt ctccaccccc gggagaccac gattatatct acaacctgga cgagagtgaa    1200
ggtgtctgtg acctctttga tgtgcctgtt ctcaacctct ga                       1242

<210> SEQ ID NO 5
<211> LENGTH: 31
<212> TYPE: DNA
<213> ORGANISM: Artificial Sequence
<220> FEATURE:
<223> OTHER INFORMATION: EcoRV restriction site

<400> SEQUENCE: 5
caacagatat catggcggag gccgggccac a                                    31

<210> SEQ ID NO 6
<211> LENGTH: 31
<212> TYPE: DNA
<213> ORGANISM: Artificial Sequence
<220> FEATURE:
<223> OTHER INFORMATION: Corresponding to nucleotides in positions
      1319-1338

<400> SEQUENCE: 6
ccattaatta agggtcccag ccacacaggg c                                    31

```
<210> SEQ ID NO 7
<211> LENGTH: 20
<212> TYPE: DNA
<213> ORGANISM: Artificial Sequence
<220> FEATURE:
<223> OTHER INFORMATION: mutation to include Ala specific codon
      compared to human E2F4
      sequence positions 742-744

<400> SEQUENCE: 7
tcagctcgct cccactgctg                                                   20

<210> SEQ ID NO 8
<211> LENGTH: 20
<212> TYPE: DNA
<213> ORGANISM: Artificial Sequence
<220> FEATURE:
<223> OTHER INFORMATION: mutation to include Ala specific codon
      compared to human E2F4
      sequence positions 742-744

<400> SEQUENCE: 8
cagtgggagc gagctgagga                                                   20

<210> SEQ ID NO 9
<211> LENGTH: 20
<212> TYPE: DNA
<213> ORGANISM: Artificial Sequence
<220> FEATURE:
<223> OTHER INFORMATION: 5? non-mutated oligonucleotide positions
      352-371

<400> SEQUENCE: 9
aaggtgtggg tgcagcagag                                                   20

<210> SEQ ID NO 10
<211> LENGTH: 20
<212> TYPE: DNA
<213> ORGANISM: Artificial Sequence
<220> FEATURE:
<223> OTHER INFORMATION: 3? non-mutated oligonucleotide positions
      1005-1025

<400> SEQUENCE: 10
ggtctgcctt gatgggctca                                                   20
```

PHOSPHORYLATION ON THE THR-248 AND/OR THR-250 RESIDUES OF TRANSCRIPTION FACTOR E2F4 AS A THERAPEUTIC TARGET IN PATHOLOGICAL PROCESSES ASSOCIATED WITH SOMATIC POLYPLOIDY

CROSS-REFERENCE TO RELATED APPLICATIONS

This application is a national stage application claiming priority to International Application No. PCT/ES2012/070795, filed Nov. 15, 2012, which claims priority to Spanish Application No. P201131892, filed on Nov. 24, 2011. The entire disclosure of each prior application is hereby incorporated by reference in its entirety.

FIELD OF THE ART

The present invention belongs to the pharmaceutical sector, relating specifically to molecular target identification for developing therapeutic tools.

PRIOR STATE OF THE ART

The association existing between cell cycle reactivation in postmitotic cells with subsequent de novo DNA synthesis and various pathological processes affecting both neurons (neurodegeneration, ischemia, etc.) and myocytes (hypertrophic cardiomyopathy, vascular pathologies associated with hypertension and aging) is known. In many cases, cell cycle reactivation does not involve cell division but rather is part of an endoreduplication mechanism (Ullah et al., 2009) which translates into the generation of somatic polyploidy (polyploidy that only affects certain cell types and is not passed on from generation to generation). Perhaps one example of a pathology associated with somatic polyploidy is Alzheimer's disease (AD). It is known that in this disease neurons reactivate the cell cycle before degenerating (Yang et al., 2003), increasing nuclear DNA content (Arendt et al., 2010). These neurons are likely to experience morphological and functional modifications compromising their survival (Frade and López-Sánchez, 2010). In fact, it has been described that hyperploid neurons are those that predominantly degenerate in the brain of patients with AD (Arendt et al., 2010). Cardiac muscle tissue also contains a percentage of polyploid myocytes, the proportion of which may be altered in pathological situations (Yabe and Abe, 1980; Vliegen et al., 1995). Vascular smooth muscle can also suffer impairments associated with polyploidy (McCrann et al. 2008). For these reasons, knowledge of the molecular base involved in endoreduplication will facilitate the design of therapeutic tools that prevent pathologies associated with somatic polyploidization. Therapeutic tools aiming to prevent somatic endoreduplication associated with human pathologies have not been developed until now, most likely because it is a very recent field of research in which new concepts are starting to emerge.

US20080139517A1 proposes administering one or more agents capable of inhibiting neuronal cell cycle progression either in an early cell cycle phase or by reducing mitogenic stimulation in age associated memory impairment (AAMI), mild cognitive impairment (MCI), AD, cerebrovascular dementia and other retrogenic neurodegenerative conditions. However, said patent document assumes that the degenerative process is associated with conventional cell cycle progression and not endoreduplication. Furthermore, this patent document does not extend the spectrum to other nervous system and heart diseases in which polyploidy-generating cell cycle reactivation has been or may be described.

It is indicated in Morillo et al., 2010, that the endoreduplication process in neurons leading to neuronal tetraploidy occurs naturally during embryonic development, giving rise to specific neuron populations that acquire a larger size, longer dendrites, and differential innervation regions in their target tissue (Morillo et al., 2010). Endoreduplication in these neurons is known to occur as a response to nerve growth factor NGF-mediated activation of neurotrophins receptor p75 ($p75^{NTR}$). These neurons duplicate their DNA and remain in a G2-like state due to the effect of neurotrophin BDNF which acts through its TrkB receptor preventing G2/M transition. Therefore, neuronal tetraploidization is known to take place during NGF-mediated nervous system development through $p75^{NTR}$, the activity of transcription factor E2F1, to re-enter the cell cycle. Those tetraploid neurons that do not receive sufficient BDNF signal try to perform mitosis followed by apoptotic death. In the brain of Alzheimer's patients, the presence of $p75^{NTR}$ and NGF in the affected regions is known. This suggests that the hyperploidy observed in the affected neurons may be caused by the same mechanism that generates tetraploid neurons during nervous system development. Reduced TrkB levels observed in advanced stages of the disease could facilitate neuronal death (see the development of this model in Frade and López-Sánchez, 2010).

Deschênes et al. 2004 makes reference to the mechanisms for regulating human intestinal epithelial cell proliferation and differentiation and indicates possible phosphorylation of transcription factor E2F4 by $p38^{MAPK}$. However, this document concludes that there is currently a need to investigate which residues of transcription factor E2F4 would be phosphorylated by $p38^{MAPK}$ as part of the mechanisms for regulating human intestinal epithelial cell proliferation and differentiation.

None of these documents identifies candidate molecules as therapeutic targets for inhibiting pathological polyploidization. Therefore, there is currently a need to prevent endoreduplication causing pathological polyploidization in postmitotic cells as a therapeutic method by means of identifying new therapeutic targets.

BRIEF DESCRIPTION OF THE INVENTION

The present invention relates to an inhibitory agent for inhibiting phosphorylation on Thr248 and/or Thr250 residues of transcription factor E2F4 by $p38^{MAPK}$, for use in the prevention and/or treatment of a pathology associated with somatic polyploidy.

Likewise, the present invention relates to a method for the prevention and/or treatment of a pathology associated with somatic polyploidy, characterized in that it comprises administering to the patient a therapeutically effective amount of an inhibitory agent for inhibiting phosphorylation on Thr248 and/or Thr250 residues of transcription factor E2F4 of SEQ ID No: 1.

Finally, the present invention relates to the use of an inhibitory agent for inhibiting phosphorylation on Thr248 and/or Thr250 residues of transcription factor E2F4 by $p38^{MAPK}$, as a therapeutic target in the prevention and/or treatment of a pathology associated with somatic polyploidy.

DETAILED DESCRIPTION OF THE INVENTION

In a preferred embodiment of the present invention, the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, is characterized in that it is a mutant form of transcription factor E2F4, the amino acid sequence of which is identified as SEQ ID No: 1 (human). Said mutant form of transcription factor E2F4 with SEQ ID No: 1 is preferably substituted in Thr248 and/or Thr250 residues with an amino acid that cannot be phosphorylated by p38$^{MAPK}$, other than glutamate or aspartate. Said amino acid that cannot be phosphorylated is more preferably alanine.

In another preferred embodiment of the present invention, the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, is characterized in that it is an E2F4 fragment comprised in SEQ ID No: 1, with identical capacity for interfering with phosphorylation of endogenous E2F4 by p38$^{MAPK}$.

In another preferred embodiment of the present invention, the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, is characterized in that it is a form of E2F4 from another species with mutations on conserved Thr residues. Said form of E2F4 from another species is preferably selected from SEQ ID No 2 (chicken) and SEQ ID No 3 (mouse) (see FIG. 1).

In another preferred embodiment of the present invention, the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, is characterized in that it is a synthetic molecule mimicking the mutant form of transcription factor E2F4 of SEQ ID No: 1, substituted with alanine on Thr248 and/or Thr250 residues.

On the other hand, the present invention relates to the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, characterized in that said somatic polyploidy occurs as a result of endoreduplication in postmitotic cells. Said postmitotic cells are preferably neurons and/or myocytes.

Additionally, the present invention relates to the inhibitory agent for inhibiting phosphorylation on Thr248 and/or Thr250 residues of transcription factor E2F4 by p38$^{MAPK}$, for use in the prevention and/or treatment of a pathology associated with somatic polyploidy, characterized in that said pathology associated with somatic polyploidy is selected from the following group: neurodegenerative disease, ischemia, hypertrophic cardiomyopathy, vascular pathology associated with hypertension and aging. Said pathology associated with somatic polyploidy is preferably a neurodegenerative disease. Said neurodegenerative disease is even more preferably Alzheimer's disease.

In another preferred embodiment of the present invention, the method for the prevention and/or treatment of a pathology associated with somatic polyploidy, which comprises administering to the patient a therapeutically effective amount of an inhibitory agent for inhibiting phosphorylation on Thr248 and/or Thr250 residues of transcription factor E2F4 of SEQ ID No: 1, is characterized in that said inhibitory agent can be comprised in either a peptide or protein associated with another cell membrane-permeable peptide facilitating the intake thereof into the cell, or else in a vector capable of infecting neurons and/or myocytes, preferably suitable for gene therapy, said vector is more preferably a viral vector, and said viral vector is even more preferably a lentivirus.

Figure 1:
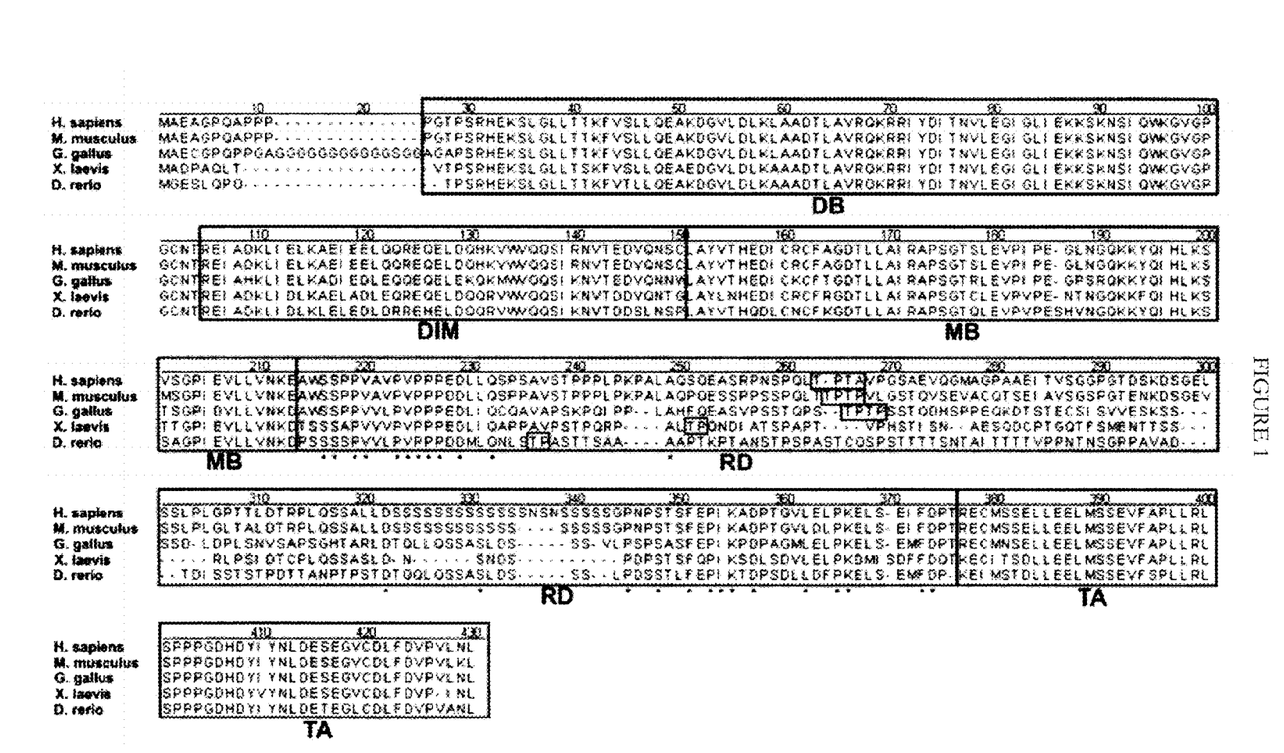
FIG. 1 shows the structure, functional domains and sequence conservation of transcription factor E2F4. The drawing illustrates the comparison between amino acid sequences of human transcription factor E2F4 (*H. sapiens*; SEQ ID NO: 1), mouse (*M. musculus*; SEQ ID NO: 2) transcription factor E2F4, chicken (*G. gallus*; SEQ ID NO: 3) transcription factor E2F4, frog *Xenopus laevis* (*X. laevis*; SEQ ID NO: 11) transcription factor E2F4 and zebrafish (*D. rerio*; SEQ ID NO: 12) transcription factor E2F4. The different known functional domains including the DNA-binding (DB) region, the dimerization (DIM) domain, the marked box (MB) and the transactivation (TA) domain are also indicated. The region including Thr248 and Thr250 residues of the human sequence conserved in other species (indicated by small rectangles) is also indicated: Thr249 and Thr251 residues in the mouse sequence, Thr261 and Thr263 residues in the chicken sequence, Thr228 residue in frog and Thr217 residue in zebrafish. This region is referred to as the regulator domain (RD). Amino acids completely conserved in the regulator domain are indicated with a dot.
Figure 2:
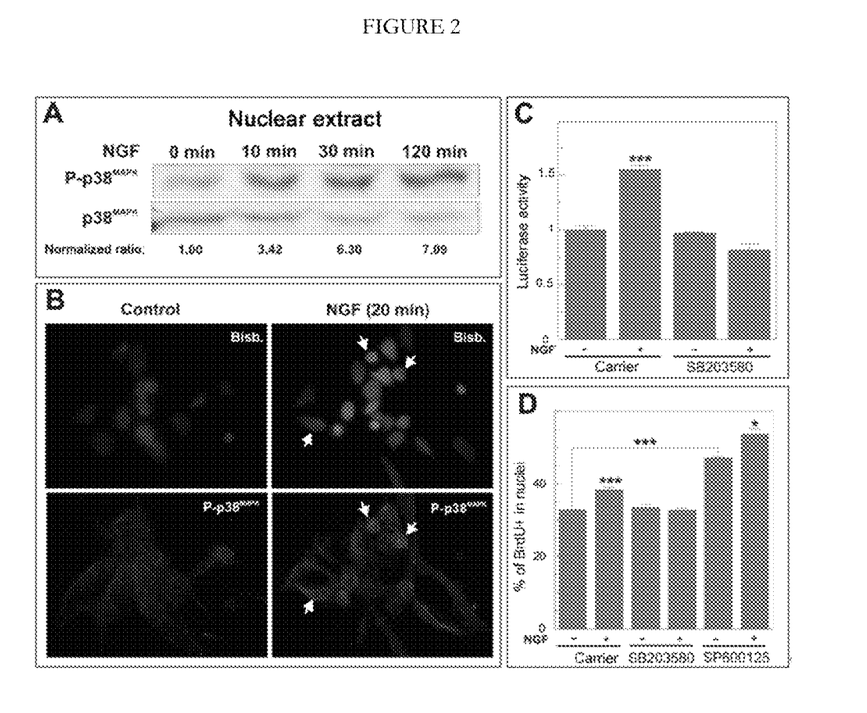
FIG. 2 shows that nuclear p38$^{MAPK}$ activation in response to NGF is necessary for cycle reactivation in chick embryo retinal cell neurogenic cultures in E6. These cells respond to NGF by inducing cell cycle reactivation that leads to somatic tetraploidy (endoreduplication) (Morillo et al., 2010). A. Western blot with anti-active p38$^{MAPK}$ (P-p38$^{MAPK}$) and anti-p38$^{MAPK}$ in nuclear extracts of the mentioned neurogenic cultures treated for the indicated time with 100 ng/ml NGF. The normalized ratios between P-p38$^{MAPK}$ and p38$^{MAPK}$ levels are indicated at the bottom. B. Immunohistochemical staining with anti-active p38$^{MAPK}$ antibodies (P-p38$^{MAPK}$) in the mentioned neurogenic cultures treated with 100 ng/ml NGF for 20 minutes. The nuclei were labeled with bisbenzimide (Bisb.). Note the signal increase in the nucleus of cells treated with NGF. C. Luciferase assay in extracts of chick embryo retinal cell neurogenic cultures E6 transfected with a plasmid expressing luciferase under the control of cMyc gene promoter, known for its response to E2F during G1/S transition, and another plasmid with the constitutive expression of β-galactosidase. The luciferase/β-galactosidase ratio values are depicted as "luciferase activity". Treatment with 100 ng/ml NGF entails cMyc promoter activation, indicating cell cycle reactivation. This effect is blocked with selective p38$^{MAPK}$ inhibitor SB203580 (used at 5 µM). D. Incorporation of BrdU to indicate entry into S phase in chick embryo retinal cell neurogenic cultures E6. Treatment with 100 ng/ml NGF entails an increase in the proportion of cells in S phase, an effect which is blocked by selective p38$^{MAPK}$ inhibitor SB203580 (used at 5 µM), but not by selective JNK inhibitor, SP600125 (used at 7 µM). *$p<0.05$; ***$p<0.005$ (Student's t-test)
Figure 3:
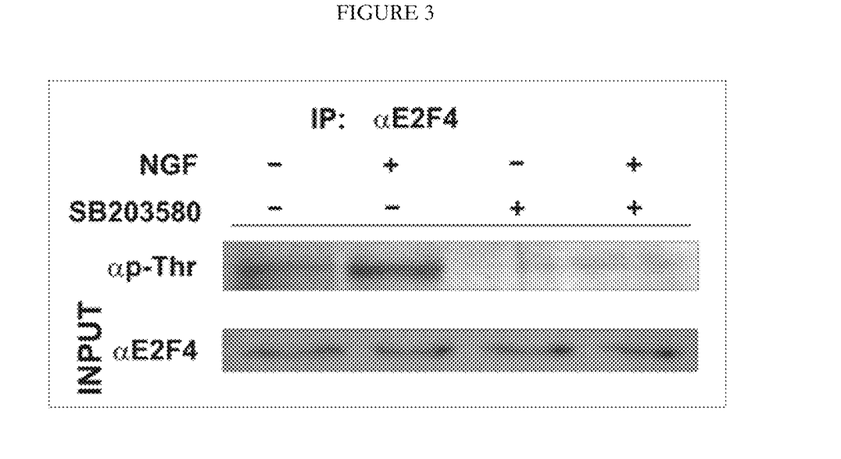

Our laboratory has unveiled the mechanism used by NGF/p75$^{NTR}$ to induce cell cycle reactivation in neurons of chicken during embryonic development, an effect which generates endoreduplication and neuronal tetraploidy (Morillo et al., 2010). Said mechanism is based on the activation of Ser/Thr kinase p38$^{MAPK}$ in the nucleus of affected cells (FIG. 2), and subsequent phosphorylation on threonine residues of transcription factor E2F4 (FIG. 3). Any other signaling pathway that activates p38$^{MAPK}$ in postmitotic cells could result in hyperploidization using transcription factor E2F4. In chicken, there are only two residues that can be phosphorylated by p38$^{MAPK}$, i.e., threonine residues Thr261 and Thr263 (FIG. 1). The use of NetPhosK 1.0 software predicts that these threonine residues are immersed in a domain conserved with human and mouse E2F4 proteins (FIG. 1). In the case of human E2F4 protein, the threonine residue that can be phosphorylated by p38$^{MAPK}$, as predicted by NetPhosk 1.0 software, is threonine residue Thr248 (the consensus site for phosphorylation by p38$^{MAPK}$ must have a consecutive Pro residue, a TP sequence, located after said threonine). Human Thr 250 residue has also been considered to be protected even though it lacks a consecutive Pro residue. The reason is its degree of conservation with mouse Thr251 threonine residue and chicken Thr263 threonine residue, both with a consecutive Pro residue and predicted by NetPhosK 1.0 software as threonine residues that can be phosphorylated by p38$^{MAPK}$.

Figure 4:
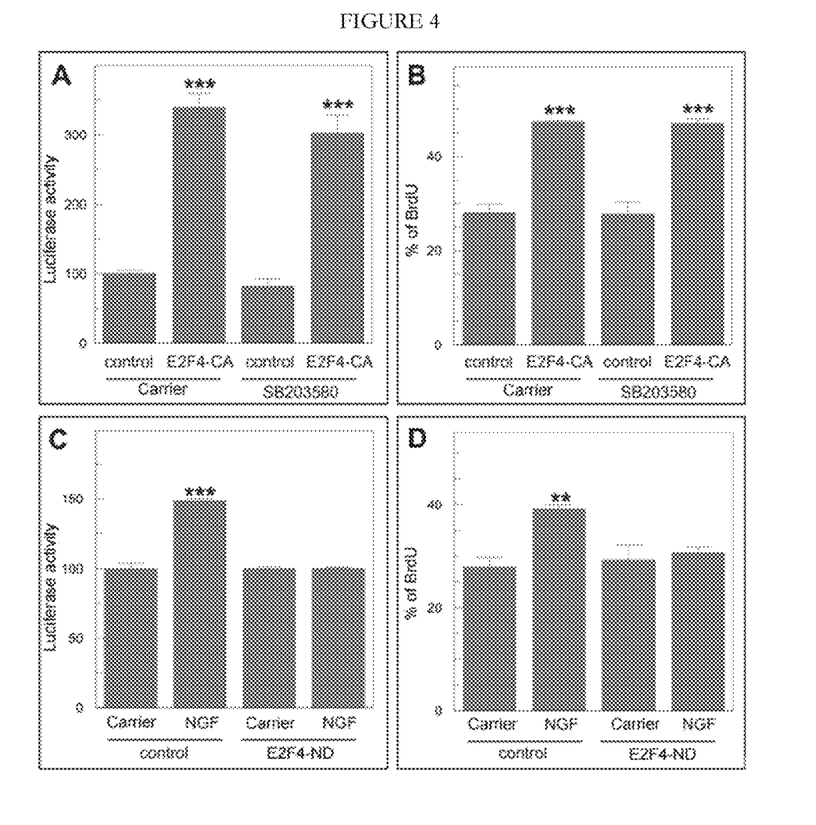
FIG. 4 shows that phosphorylation on Thr261/Thr263 residues of E2F4 is capable of inducing cycle reactivation in chick embryo retinal cell neurogenic cultures in E6. A. Luciferase activity analyzed as described in FIG. 2C. The expression of the constitutively active form of E2F4 (E2F4-CA) characterized by Thr261Glu/Thr263Glu substitutions induces cMyc promoter activity, an effect that can be observed even in the presence of selective p38$^{MAPK}$ inhibitor SB203580 (used at 5 μM). B. The incorporation of BrdU increases significantly in cells transfected with the constitutively active form of E2F4 (E2F4-CA), an effect that can be observed even in the presence of selective p38$^{MAPK}$ inhibitor SB203580 (used at 5 μM). Based on the results shown in panels A and B, it is deduced that p38$^{MAPK}$ acts exclusively through Thr261/Thr263 residues. C. Luciferase activity analyzed as described in FIG. 2C. The expression of the negative dominant form of E2F4 (E2F4-ND) characterized by Thr261Ala/Thr263Ala substitutions prevents the effect of 100 ng/ml NGF on cMyc promoter activity. D. The expression of the negative dominant form of E2F4 (E2F4-ND) prevents the effect of 100 ng/ml NGF on the incorporation of BrdU in retinal neurogenic cultures.

Phosphorylation of Thr261/Thr263 residues of E2F4 is crucial for cell cycle reactivation induced by NGF through p75$^{NTR}$ in chick embryo retinal cells in neuronal differentiation process (FIG. 4). Such cell cycle reactivation leads to neuronal tetraploidy (Morillo et al., 2010). We have observed that the use of a constitutively active form of chicken E2F4, in which Thr261 and Thr263 residues have been substituted with Glu (a positively charged amino acid mimicking the phosphorylated state of Thr) is capable of mimicking the effect of NGF on retinal neurons (FIG. 4A, FIG. 4B). It has also been demonstrated that the use of a negative dominant form of chicken E2F4 (Thr261Ala/Thr263Ala) preventing phosphorylation thereof by p38$^{MAPK}$ is capable of inhibiting the effect of NGF on the cell cycle in neurogenic retinal cultures (FIG. 4C, FIG. 4D). Therefore, it is foreseeable that the expression of this mutant form Thr261Ala/Thr263Ala (or the human form Thr248Ala/Thr250Ala) in affected neurons or myocytes associated with the pathologies described above could inhibit the endoreduplication process and the subsequent hyperploidization, which could prevent, or at least slow down, disease progression. The present invention relates to the use of said mutant forms of E2F4 for preventing hyperploidization and the associated pathological effects in various diseases affecting postmitotic cells (neurons and muscle cells).

Therefore, the present invention demonstrates that phosphorylation on conserved homologous Thr residues of Thr248 and Thr250 of human E2F4 is crucial for inducing endoreduplication in retinal neurons.

This invention also protects any method for specifically inhibiting phosphorylation on Thr248 and/or Thr250 residues of human transcription factor E2F4 (hereinafter phosphoE2F4). The inhibition of said phosphorylation would hinder the capacity of E2F4 for inducing DNA synthesis in postmitotic cells, which has clear therapeutic benefits.

The present invention also relates to any method for inhibiting p38$^{MAPK}$/phosphoE2F4 signaling, preferably by means of a mutant form of E2F4 in which the Thr 248 residue and/or Thr250 residue has/have been substituted with an Ala residue, as performed in our laboratory with chicken E2F4.

Alternatively, the present invention also relates to any other method for inhibiting p38$^{MAPK}$/phosphoE2F4 signaling, such as for example:

substitution of Thr248 and/or Thr250 residues with other amino acids that cannot be phosphorylated, use of an E2F4 fragment with identical capacity for interfering with the phosphorylation of endogenous E2F4, use of forms of E2F4 from other species with mutations on conserved Thr residues, use of synthetic molecules mimicking the mutated form of E2F4, etc.

The present invention also protects any means for specifically transferring the aforementioned mutated forms of E2F4 into affected cells, such as for example, by means of suitable vectors, peptides that can go through the cell membrane, etc.

The invention involves the following phases:

1) Generating the blocking molecule which blocks phosphorylation of human transcription factor E2F4 in target cells The molecule chosen for blocking phosphorylation on Thr248 and/or Thr250 residues of human E2F4 (whether it is the gene coding sequence for human E2F4 or E2F4 from another species, the peptide sequence of human E2F4 or E2F4 from another species, the partial gene coding sequence for human E2F4 or E2F4 from another species, the partial peptide sequence of human E2F4 or E2F4 from another species, or another molecule mimicking the region or regions of interaction between E2F4 and p38$^{MAPK}$ capable of blocking phosphorylation on Thr248 and/or Thr250 residues of human E2F4) will be generated by chemical synthesis or by means of cloning the cDNA sequence in a plasmid that can generate suitable vectors for gene therapy.

In this last case, the coding sequence must first be amplified with a heat stable enzyme with proof-reading capacity from cDNA derived from mRNA previously obtained from a cell line or from a tissue of human origin. To clone the sequence, primers in which restriction sites that are compatible with the polylinker of the vector chosen for cloning have been included, are used. Said vector is chosen based on the method used in Example 4 for introducing the chosen sequence into the target cells. Once the sequence is cloned, a standard site-directed mutagenesis process leading to the specific modification of ACT codon encoding Thr248 and/or Thr250 residues is performed in order to transform said codon into a codon specific for any amino acid except Glu or Asp. The plasmid thus generated is co-transfected into a suitable cell line capable of packaging the vector of interest.

2) Expressing the blocking molecule which blocks phosphorylation of human transcription factor E2F4 in target cells In those cells in which the p38$^{MAPK}$-E2F4 signaling pathway is active, p3$^{MAPK}$ is expected to be inhibited upon binding to the excess molecules mimicking the mutated form of E2F4, capable of interacting with p38$^{MAPK}$ but incapable of being phosphorylated. The endoreduplication process in said cells is therefore blocked. The blocking molecules can be expressed by the same target cells if they are transferred in the form of DNA (using suitable vectors such as lentivirus, for example). Alternatively, the blocking molecules can be transferred by means of peptides capable of going through the cell membrane with greater or less target cell-type specificity.

Throughout the description and claims, the word "comprises" and variants thereof do not intend to exclude other technical features, additives, components or steps. For persons skilled in the art, other objects, advantages and features of the invention will be inferred in part from the description and in part from the practice of the invention. The following drawings and examples are provided by way of illustration and they are not meant to limit the present invention.

DESCRIPTION OF THE DRAWINGS

FIG. 3 shows NGF-promoted phosphorylation on threonine residues of E2F4 in chick embryo retinal cell neurogenic cultures in E6. The top part shows a Western blot carried out with anti-phosphoThr antibodies (αp-Thr) in extracts immunoprecipitated with anti-E2F4 antibodies originating from the indicated cultures treated with different combinations of 100 ng/ml NGF and selective inhibitor SB203580 (used at 5 μM). The bottom part shows a Western blot carried out with anti-E2F4 antibodies in the same extracts without immunoprecipitation (INPUT). The presence of NGF can be seen to involve an increase in phosphorylation on threonine residues, while the presence of p38$^{MAPK}$ inhibitor inhibits such phosphorylation.

FIG. 6 shows the diagram of the E2F4 coding sequence mutagenesis process. A pair of external primers flanking restriction sites C and D (external arrows) and another overlapping pair of internal primers including in the sequence thereof the mutagenized codon of Thr248 (internal arrows) are designed. Two PCR amplification reactions are performed with DNA polymerase Pfu and the reaction products are denatured together. After renaturing the DNA, the situation indicated in the diagram is obtained, among other possibilities. Elongation with DNA polymerase Pfu creates DNA double helices with the sequences of the external primers at the ends thereof. These sequences are exponentially amplified with said primers resulting in DNA fragments with Thr248 residue mutagenized to Ala, flanked by restriction sites C and D. The sequence containing the mutation can be sub-cloned into the expression vector using restriction sites C and D for that purpose.

REFERENCES

Arendt T, Brückner M K, Mosch B, Lösche A. (2010) Selective cell death of hyperploids neurons in Alzheimer's disease. *Am. J. Pathol.* 177:15-20.

Deschênes et al. 2004 "The Nucleocytoplasmic Shuttling of E2F4 Is Involved in the Regulation of Human Intestinal Epithelial Cell Proliferation and Differentiation".

Frade J M, López-Sánchez N. (2010) A novel hypothesis for Alzheimer disease based on neuronal tetraploidy induced by p75NTR. *Cell Cycle* 9:1934-1941.

McCrann D J, Nguyen H G, Jones M R, Ravid K. (2008) Vascular smooth muscle cell polyploidy: an adaptive or maladaptive response? *J. Cell Physiol.* 215:588-592.

Morillo S M, Escoll P, de la Hera A, Frade J M. (2010) Somatic tetraploidy in specific chick retinal ganglion cells induced by nerve growth factor. *Proc. Natl. Acad. Sci. USA* 107:109-114.

Ullah Z, Lee C Y, Lilly M A, DePamphilis M L. (2003) Developmentally programmed endoreduplication in animals. *Cell Cycle* 8:1501-1509.

Vliegen H W, Eulderink F, Bruschke A V, van der Laarse A, Cornelisse C J. (1995) Polyploidy of myocyte nuclei in pressure overloaded human hearts: a flow cytometric study in left and right ventricular myocardium. *Am. J. Cardiovasc. Pathol.* 5:27-31.

Yabe Y, Abe H. (1980) Changes in DNA synthesis in significantly hypertrophied human cardiac muscle. *Adv. Myocardiol.* 1:553-563.

Yang Y, Mufson E J, Herrup K. (2003) Neuronal cell death is preceded by cell cycle events at all stages of Alzheimer's disease. *J. Neurosci.* 23:2557-2563.

EXAMPLES

The following specific examples provided in this patent document serve to illustrate the nature of the present invention. These examples are included merely for illustrative purposes and must not be interpreted as limiting the invention herein claimed. The examples described below therefore illustrate the invention without limiting the field of application thereof.

Example 1

Cloning Human E2F4 Coding Sequence

Figure 5:
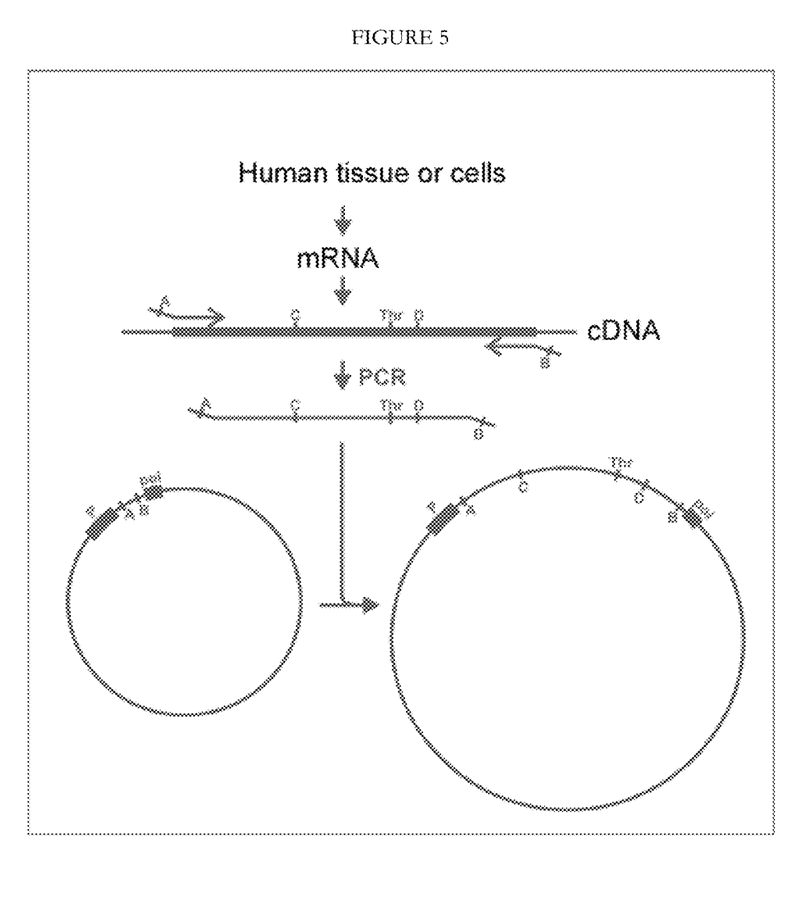
FIG. 5 shows the diagram of the method for cloning E2F4 coding sequence into a plasmid that allows generating a suitable vector for gene therapy (lentivirus, etc.), for example. The mRNA obtained from human tissue or cells is converted into cDNA using reverse transcriptase. The human E2F4 coding sequence is depicted as a gray rectangle in which the position of the codon encoding Thr 248 residue is indicated. This codon is flanked by two specific restriction sites (C and D). Two primers are designed based on the sequence of the ends of the coding region with a specific restriction site at the 5' ends (A and B) thereof. These targets also appear in the polylinker of the expression vector and are used for cloning the E2F4 coding sequence into said vector. P: promoter responsible for the transcription of E2F4 protein. pol: polyadenylation sequence used for introducing a poly(A) tail in the mRNA generated by the vector.

Human E2F4 coding sequence (positions 64-1305 of the sequence with NCBI accession number: NM_001950) (SEQ ID No 4) is cloned into a plasmid that can generate suitable vectors for gene therapy (lentiviral vectors, for example). The coding sequence must be previously amplified with DNA polymerase enzyme Pfu from cDNA derived from mRNA previously obtained from a cell line or from a tissue of human origin. To clone the sequence, primers including EcoRV and PacI restriction sites (underlined in the sequences indicated at the end of this paragraph) that are compatible with the polylinker of lentiviral expression vector are used (see a simple diagram of said vector in FIG. 5, the EcoRV site would correspond to A and the PacI site would correspond to B in said diagram). Examples of these oligonucleotides are as follows:

```
SEQ ID No 5: 5' oligo:
5'-CAACAGATATCATGGCGGAGGCCGGGCCACA-3'

SEQ ID No 6: 3' oligo:
5'-CCATTAATTAAGGGTCCCAGCCACACAGGGC-3'
```

The first one corresponds to nucleotides in positions 64-83 and the second one is complementary to nucleotides in positions 1319-1338 of the human E2F4 sequence.

The amplicon thus obtained is cloned into pGEM-Teasy vector (Promega) which does not have EcoRV or PacI restriction sites, in which site-directed mutagenesis described in Section 2 will be performed.

Example 2

Mutating Thr248 Residue (Thr250 Residue can be Mutated by Means of a Similar Method Once the Thr248Ala Mutation is Generated)

Once the human E2F4 sequence is cloned into the pGEM-Teasy vector, oligonucleotides are designed in the region comprised between positions 731-754 of human E2F4 coding sequence, corresponding to SEQ ID No 4.

These oligonucleotides include ACT codon encoding Thr248 residue (in positions 742-744 of human E2F4 coding sequence) that is mutated as Ala specific codon (GCT sequence). Examples of these oligonucleotides are:

```
SEQ ID No 7: 5' mutated oligo:
5'-TCAGCTCGCTCCCACTGCTG-3' (positions 735-754).

SEQ ID No 8: 3' mutated oligo:
5'-CAGTGGGAGCGAGCTGAGGA-3' (positions 732-751).
```

Figure 6:
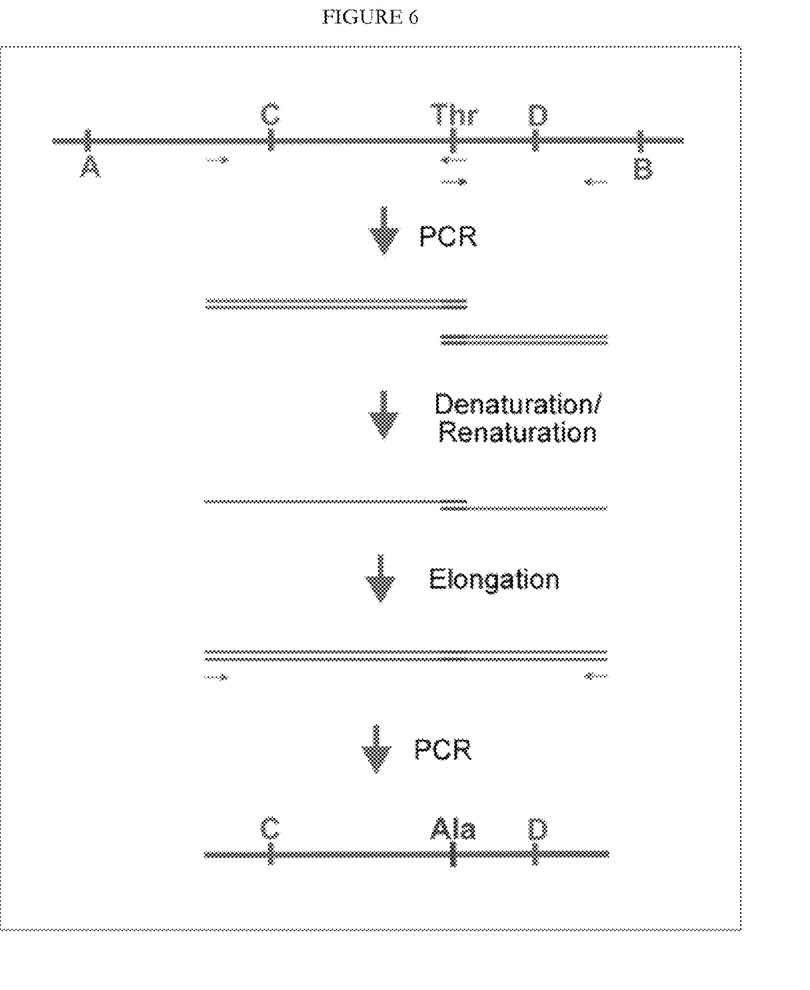

These oligonucleotides (containing the underlined mutation) will be used as primers of two independent reactions indicated in FIG. 6. Another pair of primers flanking enzyme BspEI restriction sites (indicated as C and D in FIG. 6) is designed for these reactions. The cDNA sequence encoding human E2F4 include two BspEI sites in positions 374-379 and 979-984 with TCCGGA sequence. Examples of these primers are:

```
SEQ ID No 9: 5' non-mutated oligo:
5'-AAGGTGTGGGTGCAGCAGAG-3' (position 352-371)
```

```
SEQ ID No 10: 3' non-mutated oligo:
5'-GGTCTGCCTTGATGGGCTCA-3' (position 1005-1025)
```

Two PCR amplification reactions are subsequently performed with DNA polymerase Pfu as indicated in the diagram of FIG. 6 (5' non-mutated oligo with 3'mutated oligo and 5'mutated oligo with 3' non-mutated oligo), and the reaction products are denatured together. After renaturing the DNA, the situation indicated in the diagram of FIG. 6 is obtained, among other possibilities. Elongation of these hybrids with DNA polymerase Pfu creates DNA double helices that can be amplified with external primers (5' non-mutated oligo and 3' non-mutated oligo; see FIG. 6). DNA fragments with Thr248 residue mutagenized to Ala, flanked by restriction sites C and D (see FIG. 6), are therefore obtained. The sequence containing the mutation can then be sub-cloned into pGEM-Teasy plasmid generated in point 1, using restriction sites C and D (BspEI) for that purpose. After sequencing the modified clones, a clone in which the sequence has been incorporated in the suitable orientation is selected.

Example 3

Generating Vectors for Therapy that can Infect the Nervous System pGEM-Teasy plasmid with the mutated human E2F4 coding sequence (T248A) is cleaved with EcoRV and PacI enzymes to release said sequence and is sub-cloned into the polylinker of the lentiviral expression vector pSMPUW-Hygro (Cell Biolabs, Inc.) containing the EcoRV and PacI sites. The vector thus generated is co-transfected into a suitable cell line capable of packaging the vector of interest.

Example 4

Expressing the Mutated Form of E2F4 in Target Cells

In those neurons or myocytes in which the $p38^{MAPK}$-E2F4 signaling pathway is active, $p38^{MAPK}$ is expected to be inhibited upon binding to an excess of mutated E2F4 molecules, similarly to that observed in neurons treated with NGF in the differentiation process. The endoreduplication process in said cells is thus blocked. Given that phosphorylation on Thr248 residue of E2F4 does not take place in other cell functions with the exception of endoreduplication, its presence in other cells should not have side effects.

The invention claimed is:

1. A method for treating a neurodegenerative condition associated with somatic polyploidy resulting from endoreduplication in post-mitotic cells in a patient, wherein said method comprises administering to the patient a therapeutically effective amount of an inhibitory agent for inhibiting phosphorylation on Thr248 and/or Thr250 residues of transcription factor E2F4 by $p38^{MAPK}$, wherein the inhibitory agent is a mutant form of transcription factor E2F4 comprising the amino acid sequence of SEQ ID No: 1 substituted on Thr248 and/or Thr250 residues with an amino acid that cannot be phosphorylated by $p38^{MAPK}$, or a nucleotide sequence encoding said mutant form.

2. The method according to claim 1, characterized in that said amino acid that cannot be phosphorylated is alanine.

3. A method for treating a neurodegenerative condition associated with somatic polyploidy resulting from endoreduplication in post-mitotic cells in a patient, wherein said method comprises administering to the patient a therapeutically effective amount of an inhibitory agent for inhibiting phosphorylation on Thr248 and/or Thr250 residues of transcription factor E2F4 by $p38^{MAPK}$, wherein the inhibitory agent is a mutant form of transcription factor E2F4 comprising the amino acid sequence of SEQ ID No 2 substituted on Thr249 and/or Thr251 residues with an amino acid that cannot be phosphorylated by $p38^{MAPK}$, a mutant form of transcription factor E2F4 comprising the amino acid sequence of SEQ ID No 3 substituted on Thr261 and/or Thr263 residues with an amino acid that cannot be phosphorylated by $p38^{MAPK}$, or a nucleotide sequence encoding said mutant form.

4. The method according to claim 1, wherein said post-mitotic cells are neurons and/or myocytes.

5. The method according to claim 3, characterized in that said postmitotic cells are neurons and/or myocytes.

6. The method according to claim 1, characterized in that said neurodegenerative disease is Alzheimer's disease.

7. The method according to claim 1, characterized in that the inhibitory agent is fused to or conjugated to a peptide or a protein associated with another cell membrane-permeable peptide facilitating the incorporation thereof into the cell.

8. The method according to claim 1, characterized in that the inhibitory agent is encoded by DNA and included in a vector capable of infecting neurons and/or myocytes.

9. The method according to claim 8, characterized in that said vector is a viral vector.

10. The method according to claim 9, characterized in that said viral vector is a lentivirus.

11. The method according to claim 3, characterized in that said neurodegenerative disease is Alzheimer's disease.

12. The method according to claim 3, characterized in that said inhibitory agent is fused to or conjugated to a peptide or a protein associated with another cell membrane-permeable peptide facilitating the incorporation thereof into the cell.

13. The method according to claim 3, characterized in that said inhibitory agent is encoded by DNA and included in a vector capable of infecting neurons and/or myocytes.

14. The method according to claim 13, characterized in that said vector is a viral vector.

15. The method according to claim 14, characterized in that said viral vector is a lentivirus.

16. The method according to claim 3, characterized in that said amino acid that cannot be phosphorylated is alanine.

\* \* \* \* \*